(12) United States Patent
Pachal

(10) Patent No.: US 6,176,835 B1
(45) Date of Patent: Jan. 23, 2001

(54) BIOPSY METHOD AND DEVICE

(75) Inventor: Murray Pachal, Whangarei (NZ)

(73) Assignee: Murray Pachal Family Trust (NZ)

( * ) Notice: Under 35 U.S.C. 154(b), the term of this patent shall be extended for 0 days.

(21) Appl. No.: 09/446,818

(22) PCT Filed: Jun. 26, 1998

(86) PCT No.: PCT/NZ98/00091

§ 371 Date: Dec. 23, 1999

§ 102(e) Date: Dec. 23, 1999

(87) PCT Pub. No.: WO99/00056

PCT Pub. Date: Jan. 7, 1999

(30) Foreign Application Priority Data

Jun. 27, 1997 (NZ) ................................................ 328199

(51) Int. Cl.$^7$ .................................................. A61B 10/00
(52) U.S. Cl. ........................... 600/567; 604/116; 378/37; 382/123
(58) Field of Search .................................... 600/564, 566, 600/439, 443; 604/116, 117; 378/37, 42; 382/132

(56) References Cited

U.S. PATENT DOCUMENTS

| 4,651,732 | 3/1987 | Frederick . |
| 4,821,727 | 4/1989 | Levene et al. . |

FOREIGN PATENT DOCUMENTS

| WO93/15660 | 8/1993 | (WO) . |
| WO93/17620 | 9/1993 | (WO) . |

*Primary Examiner*—Max Hindenburg
*Assistant Examiner*—Pamela L Wingood
(74) *Attorney, Agent, or Firm*—D. Peter Hochberg; Katherine R. Vierya; William H. Holt

(57) ABSTRACT

This invention relates to a method of performing accurate biopsies, particularly core breast biopsies, and a device for facilitating the accuracy of the taking of biopsies. The device involves the provision of guiding members or wing-type projections on at least two sides of the barrel of a biopsy gun. Each guiding member is parallel to the axis of a biopsy needle attached to the gun and there are at least two guiding members projecting from the barrel of the gun substantially perpendicular to one another. Each guiding member is preferably in line with the needle, so that in use the biopsy needle is in the plane of each guiding member. The device may be in the form of a biopsy gun with the guiding members integrally formed or affixed, or it may be in the form of an attachment for attaching to a conventional biopsy gun. The method of the invention involves a means of guiding a biopsy needle to a calculated site of a target lesion; identifying a location on the skin surface directly between the calculated site and a source of electromagnetic radiation, including a light source; positioning a biopsy needle tip at that location; monitoring shadows on the skin surface created by guiding members on a biopsy gun to which the biopsy needle is attached, each guiding member projecting from a side of the biopsy gun, in a parallel axis to the needle attached or held by the gun, and at least two of the guiding members substantially perpendicular to one another; and guiding the biopsy needle to the calculated site by minimizing the shadows so that the needle remains substantially parallel to the electromagnetic radiation beam.

14 Claims, 3 Drawing Sheets

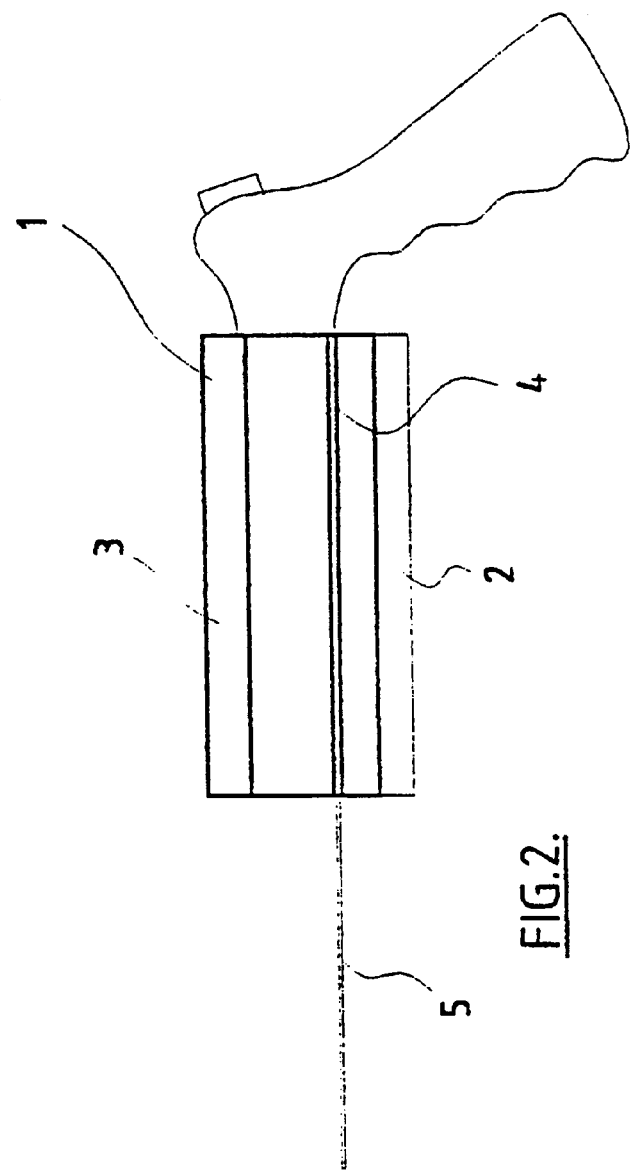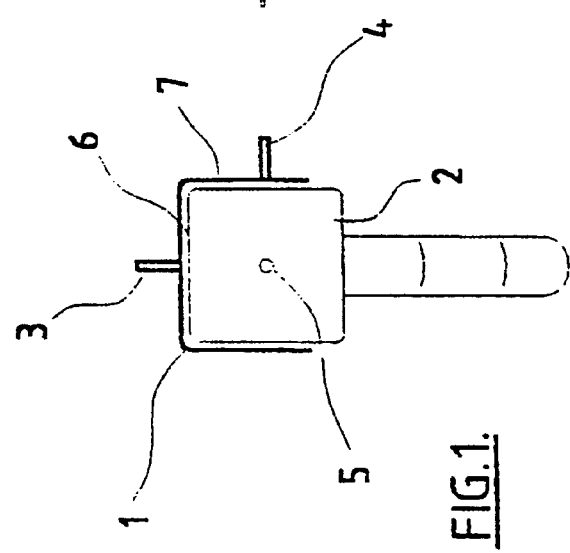

BIOPSY METHOD AND DEVICE

TECHNICAL FIELD

This invention relates to a method and apparatus for facilitating biopsies, and particularly core breast biopsies.

BACKGROUND

A critical issue in the conducting of core biopsies is the accurate location of suspect tissue (hereinafter referred to as a lesion), and thereafter the accurate guiding of the biopsy needle to the lesion. Sophisticated methods and apparatus have been developed for core biopsies in connection with mammography.

Stereotactic breast biopsy involves the taking of a first radiographic image of a lesion in a breast, moving the breast or x-ray tube a known distance and then taking a second radiographic image of the lesion in the breast, so that the x, y and z coordinates of the lesion site in the breast may be calculated.

Once the location of the lesion has been confirmed, most biopsy needles and their associated biopsy guns are computer-controlled to drive the biopsy needle to the calculated position in the breast. The use of such equipment is expensive and time consuming, and cannot be justified in small practices.

New methods are required which avoid the high cost associated with computer-controlled equipment, and which may be conducted relatively quickly and efficiently, whilst maintaining accuracy of the biopsy.

Thus, it is an object of the present invention to provide a method and apparatus for core biopsies which reduces the abovementioned problems or at least which provides the public with a useful alternative.

Other objects of the present invention may become apparent from the following description which is given by way of example only.

STATEMENT OF INVENTION

According to one aspect of the present invention there is provided a biopsy method wherein a biopsy needle is guided to a calculated site of a target lesion, said method including the steps of:

identifying a location on the skin surface directly between the calculated site and a source of electromagnetic radiation, including a light source, positioning a biopsy needle tip at the location, monitoring shadows in the light from the light source on the skin surface, created by at least two guiding members on a biopsy gun to which the biopsy needle is attached, each said guiding member projecting from a side of the biopsy gun, in a parallel axis to the needle and at least two of the guiding members substantially perpendicular to one another, and guiding the biopsy needle to the calculated site by minimising the shadows so that the needle remains substantially parallel to the electromagnetic radiation beam.

In a preferred method the biopsy needle may be in the plane of each guiding member such that the shadows are monitored in line with the needle.

In a preferred form of method of the present invention the electromagnetic radiation may be x-rays.

Preferably, the site of the target lesion may be calculated by stereotactic radiography.

In a further preferred form a biopsy method of the present invention may further comprise locating said biopsy needle at the location using a locator means.

According to a further aspect of the present invention there is provided a biopsy gun, said gun having at least two guiding members, each said guiding member projecting from a side of the biopsy gun, in a parallel axis to a needle attached to or held by the biopsy gun when in use, and each, or at least two, of said guiding members substantially perpendicular to one another.

In a further aspect of the present invention there is provided a biopsy gun attachment, securely attachable to a biopsy gun, said attachment having at least two guiding members, each said guiding member projecting from the gun attachment such that when the gun attachment is securely engaged on a biopsy gun the guiding members are in an axis parallel to a needle attached to or held by the biopsy gun when in use, and each, or at least two, of the guiding members are substantially perpendicular to one another.

Preferably, there may be two guiding members, substantially perpendicular to one another.

Preferably, each said guiding member may run substantially the length of the biopsy gun or the biopsy gun attachment.

Preferably, each guiding member may be in line with said needle, when attached to the biopsy gun, such that the needle would be in the plane of each guiding member.

In a further aspect of the invention there is provided a biopsy gun attachment including:

engagement means adapted to securely engage the biopsy gun attachment to a barrel of a biopsy gun, a first guiding member projecting from the attachment, parallel to the axis of the barrel and extending substantially the length of the barrel, and at least one further guiding member projecting from the attachment, parallel to the axis of the barrel and extending substantially the length of the barrel, the or at least one of the further guiding members substantially perpendicular to the first guiding member, and each guiding member in line with a needle attached to or held by the biopsy gun when in use, such that the needle is in the plane of each guiding member.

Other aspects of the present invention may become apparent from the following description which is given by way of example only and with reference to the accompanying drawings.

BRIEF DESCRIPTION OF DRAWINGS

FIG. 1: Shows a front view of a winged guide of the present invention in one preferred form engaged on a biopsy gun;

FIG. 2: Shows a side view of the winged guide of FIG. 1;

DETAILED DESCRIPTION OF INVENTION

Figure 4:
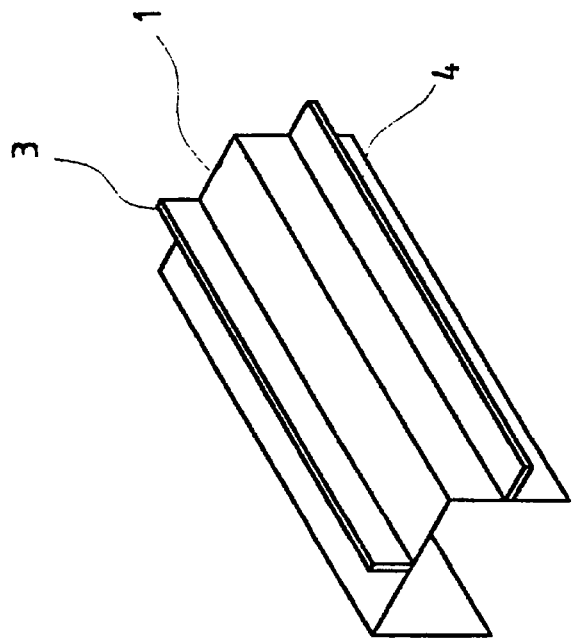
FIG. 4: Shows a perspective view of a winged guide of FIGS. 1 and 2 removed from the biopsy gun.
Figure 3:
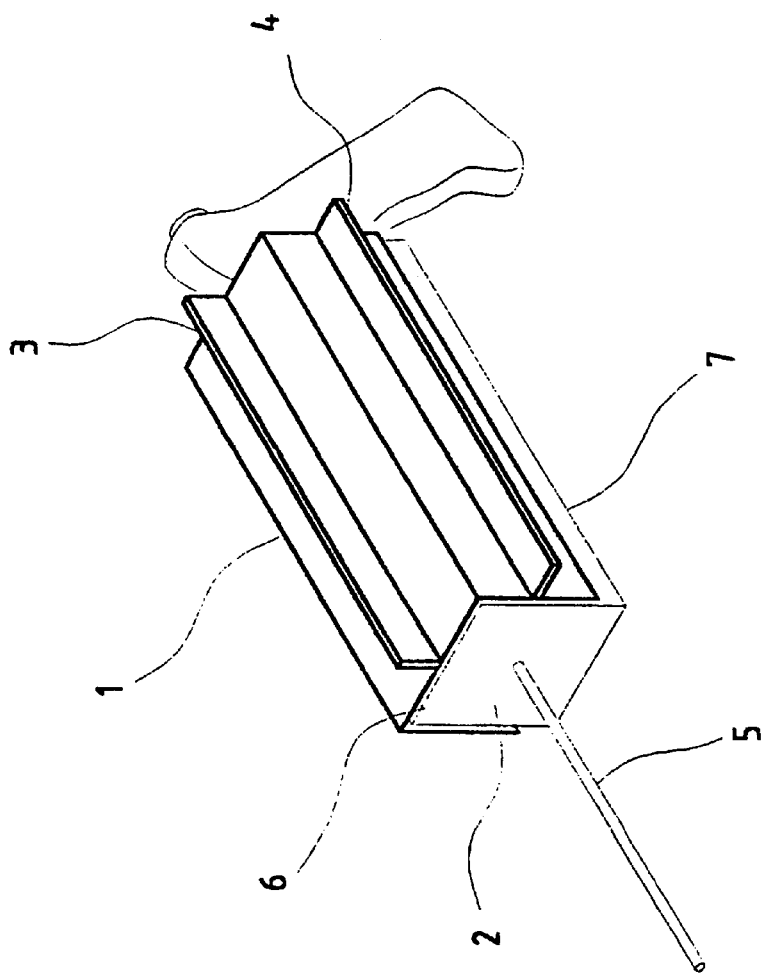
FIG. 3: Shows a perspective view of a winged guide of FIGS. 1 and 2 positioned on a biopsy gun.

The apparatus of the present invention involves the use of winged guides for a biopsy gun, as shown in FIGS. 1–4. A winged guide 1 may be in the form of a clip-on device adapted to securely engage with a biopsy gun 2. The winged guide 1 has a first wing 3 in one plane and a second wing 4 in a plane at 90° to the plane of the first wing 2. Each wing extends substantially the length of the biopsy gun 2. The winged guide 1 is constructed such that when positioned on a biopsy gun the first 3 and second 4 wings are at 90° to one another and both are in line with the position of the needle 5 in the biopsy gun 2, i.e. if the needle is positioned centrally at the end of the biopsy gun then the first wing 3 is positioned half way along a first side 6 of the biopsy gun 2, whilst the second wing 4 is positioned half way along an adjacent side 7 of the biopsy gun 2.

In the example shown in FIG. 4 the winged guide 1 is an elongate structure having three sides, and adapted to securely engage on a biopsy gun having a square or rectangular cross-section. It will be appreciated that the winged guide 1 may be temporarily or permanently affixed to the biopsy gun. Furthermore, it will also be appreciated that biopsy guns may be manufactured with the required wings integrally formed.

Winged guides or biopsy guns with wings must include at least two wings in different planes to provide the required means of accurately monitoring the direction of the biopsy needle. Further wings could also be employed, but would not be essential.

The winged guide or wings of a biopsy gun enable the biopsy needle to be accurately guided in relation to a light source. Standard mammography equipment includes a light source having a focal point at the same point as the x-ray source. By providing wings on the biopsy gun, the projection of the needle can be adjusted to minimise shadowing of the wings, at which time the needle projection will be parallel to the x-ray beam.

Figure 6:
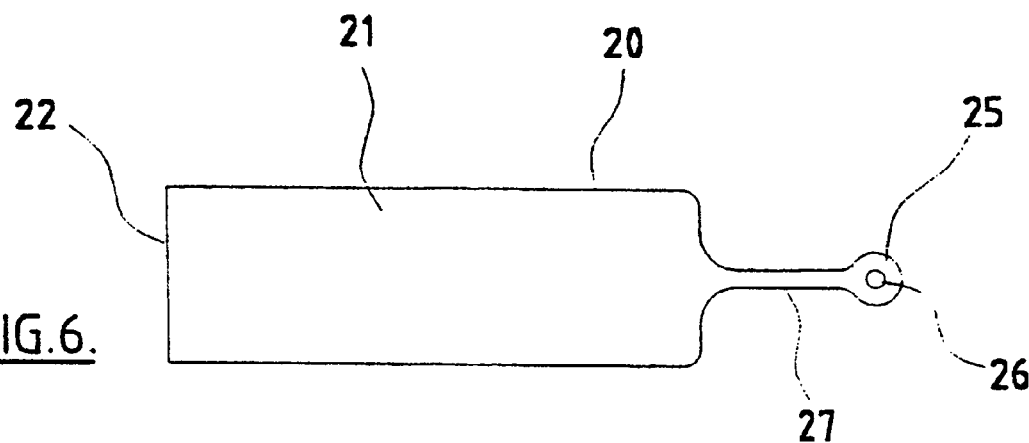
FIG. 6: Shows a plan view of a needle locator employed in the method of the present invention.
Figure 7:
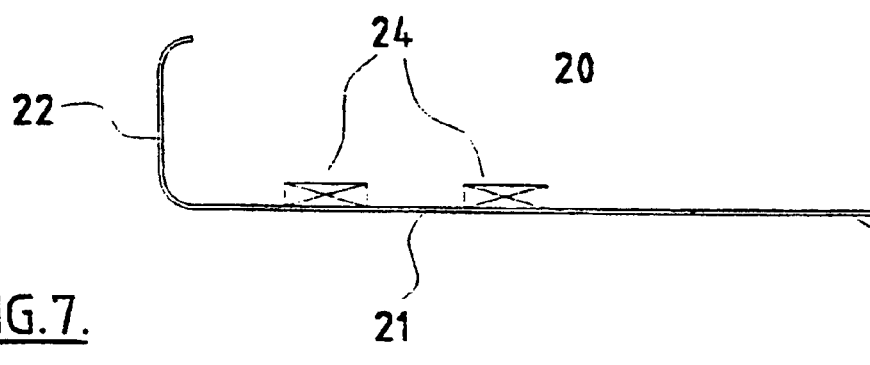
FIG. 7: Shows a side view of the locator of FIG. 6.

To further facilitate the accuracy of biopsy using a handheld biopsy gun with wings or a winged guide, a needle locator 20 may be positioned on the skin surface directly between the calculated position of a lesion and the x-ray and light source. An example of such a needle locator 20 is presented in FIGS. 6 and 7. The needle locator 20 may comprise a substantially flat strip 21 of material having a handle end 22 and a needle guiding end 23, with means for securely engaging the needle locator to a fixed object. The securing means 24 may, for example, be magnets positioned on the strip between the ends of the needle locator, sufficiently strong to ensure secure engagement of the device to a fixed object, such as a part of the holding device. The needle guiding end 23 may comprise a small metallic ring 25 having a hole 26 in the centre marginally larger than the diameter of the required biopsy needle. This ring may be connected to the rest of the needle guide by a thin rod 27, so that the needle locator 20 as a whole interferes as little as possible with the biopsy procedure.

In an alternative form the needle guiding end of the needle locator may comprise a disc having a plurality of holes, each hole marginally larger than the diameter of a biopsy needle. This form of needle locator would facilitate multiple biopsies.

The biopsy method of the present invention will now be described, as applied to a core breast biopsy, and with reference to a winged guide on the biopsy gun and the optional use of a needle locator.

The method first employs calculation of the depth of a lesion in the breast by a conventional stereotactic breast biopsy method. Thus, a holding device is employed enabling movement of the patient and breast a set amount or angling the x-ray tube a set amount in relation to the breast, such that radiographic images may be taken of the breast from two angles or directions. During imaging the breast is positioned between base and top compression plates of the holding device. The result of the two x-rays is an x-ray film with two images, with the target lesion a set distance apart. The height of the lesion above the base plate is directly correlated with the image separation, and this relationship is calibrated for each particular device and the set movement between x-rays. Thus, the height of the lesion above the base plate is calculated by measuring the separation of the two lesion images and referring to the calibration graph of height above base plate versus image separation.

The depth of the lesion below the top compression plate can then be determined by subtracting the height of the lesion above the base plate from the measured height of the top plate above the base plate.

Once the lesion depth has been calculated, the position of the lesion in the x, y plain (this being the plain of the top compression plate) is confirmed on one of the stereotactic views. Either of the two views can be used for this, but once that view has been selected then it is used during all subsequent needle insertions and calculations (this view is referred to as the "biopsy projection"). In this biopsy projection a local anaesthetic needle is inserted into the breast approximately parallel to the light beam (i.e. the hub of the syringe is maintained central over the shadow of the needle during insertion of the needle), over the anticipated position of the lesion. The lesion depth is confirmed by inserting the local anaesthetic needle to the calculated lesion depth and performing a further pair of stereotactic views. When the needle is at the correct depth there is no apparent movement of the needle tip in relation to the lesion between the two x-ray views.

Following confirmation of the calculated lesion depth, the breast is returned to the biopsy projection. With the local anaesthetic needle maintained in position, the distance between the needle shaft and the centre of the target lesion in the x, y plain is calculated on the biopsy projection. This distance is transposed onto the skin surface and a small nick is made in the skin at the correct distance from the local anaesthetic needle entrance mark. The extrapolation of the measured distance between the target lesion and the anaesthetic needle tip to the required distance between the anaesthetic needle shaft and calculated biopsy needle entry point at the skin surface may employ reference to a calibration chart taking into consideration the geometric magnification of the radiography equipment employed and the lesion depth in the breast.

A self-retaining skin retractor is then positioned in the nick to hold the incision open before the ring of a needle locator, as described above, is positioned over the incision opening. The body of the needle locator may be positioned on the upper surface of the top compression plate. The ring of the needle locator is then either slightly above or slightly below the skin surface depending on the extent to which the breast tissue herniates through the aperture in the top compression plate through which the biopsy procedure is performed. A further x-ray is then taken to confirm the correct position of the needle locator over the lesion. If the incision has been made in the correct spot, and the needle locator has been correctly positioned, then the target lesion will appear centred in the ring of the needle locator. If the image of the ring is not superimposed over the lesion on the x-ray film then adjustments can be made in accordance with calculations from that x-ray film.

Figure 5A:
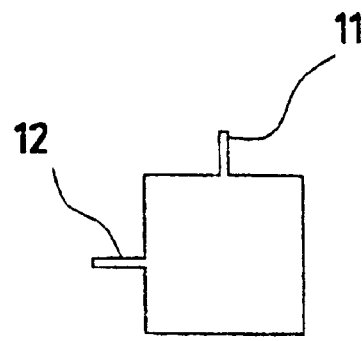
FIG. 5: Shows a schematic representation of the shadow formed from a winged guide of the present invention when engaged on a biopsy gun (a) with the gun correctly positioned parallel to the light and x-ray beams, and (b) with the gun inaccurately aligned.
Figure 5B:
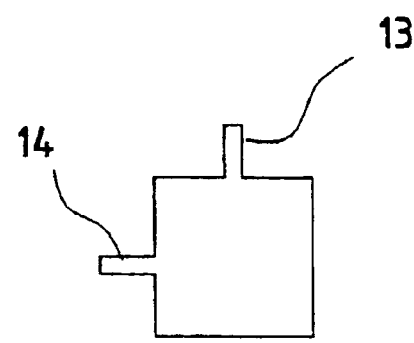

With the needle locator correctly positioned over the lesion the biopsy needle, attached to a biopsy gun with winged guide, is inserted through the ring. The operator adjusts the projection or angle of the needle to be parallel to the line of the x-ray beam by monitoring the shadow of the wings of the winged guide on the skin surface. With reference to FIG. 5, if the needle (not visible) is parallel to the line of the x-ray (also the source of light) then the wing shadows 11, 12 will be at their narrowest (as in FIG. 5a), whilst if the needle is not parallel to the x-ray beam the shadows 13, 14 of one or both wings will be broader (as in FIG. 5b). With the shadows at their narrowest the needle is inserted to the correct depth (generally 8 mm proximal to the lesion for the needle tip using standard 22 mm excursion long-throw core biopsy guns), the depth being calculated from markings on the needle itself in relation to the position of the ring of the needle locator which is at a fixed, known height.

It will be appreciated, from this description, that the wings of the biopsy gun should be substantially at right angles to one another and in line with the longitudinal axis of the needle for the method to achieve the required accuracy.

It will also be appreciated that the needle locator is an optional feature which provides a further means for improving the accuracy of biopsy. However, once the location of a lesion has been confirmed and its x, y position, in relation to the direction of the x-ray beam, transposed to the skin surface, then the biopsy needle may be guided by the wings on the biopsy gun without the need for the needle locator. In such circumstances the depth of the biopsy is determined in relation to the skin surface.

With the needle in position the biopsy gun is fired to obtain the required sample. Several samples may be taken through the same skin incision, with an x-ray image taken between each sample, and the needle locator position adjusted. Thus, all regions of a lesion may be appropriately sampled.

Employing this method the accuracy of the biopsy in the x, y plane is within about 0.5 mm. The biopsy gun wings reveal a widening of the shadow even with movement of 1–2 mm at the hand-held end of the biopsy gun. Such movement would equate with movement of the needle tip 0.1–0.2 mm when at a depth of 3 cm beneath the skin surface.

Thus, the biopsy method described, including the use of a guide members or wings on the biopsy gun and optionally a needle locator, enables accurate stereotactic breast biopsies without the need for expensive and time consuming computer-controlled devices.

The method and apparatus of the invention have been described with specific reference to breast biopsies, but persons skilled in the art will appreciate that the use of wings on a biopsy gun to facilitate accurate guiding of the biopsy needle has application in other types of biopsy. Such persons will also appreciate that the method and apparatus may be employed with forms of radiation for locating lesions other than x-rays, for example, magnetic resonance imaging.

Where in the foregoing description reference has been made to specific components and integers of the invention having known equivalents then such equivalents are herein incorporated as if individually set forth.

Although the invention has been described by way of example, and with particular reference to the preferred embodiments shown in the accompanying drawings, it should be appreciated that variations and modifications may be made thereto, without departing from the scope of the invention.

What is claimed is:

1. A biopsy method in which a biopsy needle is guided from the skin surface to a calculated site of a target lesion, the method including the steps of:

identifying a location on the skin surface directly between the calculated site and a source of electromagnetic radiation, including a light source, positioning a biopsy needle tip at the location, monitoring shadows in the light from the light source on the skin surface, created by at least two guiding members on a biopsy gun to which the biopsy needle is attached, each guiding member projecting from a side of the biopsy gun, in a parallel axis to the needle and at least two of the guiding members substantially perpendicular to one another, and guiding the biopsy needle to the calculated site by minimising the shadows so that the needle remains essentially parallel to the electromagnetic radiation beam.

2. A biopsy method according to claim 1 wherein the biopsy needle is in the plane of each wing and the shadows are monitored in line with the needle.

3. A biopsy method according to claim 1 wherein the electromagnetic radiation is x-rays.

4. A biopsy method according to claim 1 wherein the site of the target lesion is calculated by stereotactic radiography.

5. A biopsy method according to claim 1 further including the step of locating the biopsy needle at the location using locator means.

6. A biopsy gun having at least two guiding members, each said guiding member projecting from a side of the biopsy gun, in a parallel axis to a needle attached or held by the biopsy gun when in use, and each, or at least two, of the guiding members projecting from sides of the gun substantially perpendicular to one another.

7. A biopsy gun according to claim 6 having two guiding members, substantially perpendicular to one another.

8. A biopsy gun according to claim 7 wherein each guiding member extends substantially the length of the biopsy gun.

9. A biopsy gun according to claim 8 wherein each guiding member is in line with a needle attached to or held by the biopsy gun when in use, such that the needle would be in the plane of each guiding member.

10. A biopsy gun attachment, securely attachable to a biopsy gun, said attachment having at least two guiding members, each said guiding member projecting from the gun attachment such that when the gun attachment is securely engaged on a biopsy gun the guiding members are in an axis parallel to a needle attached to or held by the biopsy gun when in use, and each, or at least two, of the guiding members are substantially perpendicular to one another.

11. A biopsy gun attachment according to claim 10 wherein there are two guiding members, substantially perpendicular to one another.

12. A biopsy gun attachment according to claim 11 wherein each guiding member extends substantially the length of the biopsy gun attachment.

13. A biopsy gun attachment according to claim 12 wherein when the attachment is securely attached to a biopsy gun each guiding member is in line with a needle attached to or held by the biopsy gun when in use, such that the needle is in the plane of each guiding member.

14. A biopsy gun attachment including:

engagement means adapted to securely engage the biopsy gun attachment to a barrel of a biopsy gun, a first guiding member projecting from the attachment, parallel to the axis of the barrel and extending substantially the length of the barrel, and at least one further guiding member projecting from the attachment, parallel to the axis of the barrel and extending substantially the length of the barrel, the or at least one of the further guiding members substantially perpendicular to the first guiding member, and each guiding member in line with a needle attached to or held by the biopsy gun when in use, such that the needle is in the plane of each guiding member.

* * * * *